(12) United States Patent
Wall

(10) Patent No.: US 9,249,588 B2
(45) Date of Patent: Feb. 2, 2016

(54) HYBRID OPERATING ROOM FOR COMBINED SURGICAL AND FIXED IMAGING SERVICES IN AN AMBULATORY SURGICAL CENTER

(71) Applicant: L. Philipp Wall, Paradise Valley, AZ (US)

(72) Inventor: L. Philipp Wall, Paradise Valley, AZ (US)

(73) Assignee: PM HOLDINGS, Paradise Valley, AZ (US)

( * ) Notice: Subject to any disclaimer, the term of this patent is extended or adjusted under 35 U.S.C. 154(b) by 0 days.

(21) Appl. No.: 14/219,880

(22) Filed: Mar. 19, 2014

(65) Prior Publication Data

US 2015/0267427 A1    Sep. 24, 2015

(51) Int. Cl.
*E04H 3/08* (2006.01)
*G21F 7/00* (2006.01)
(Continued)

(52) U.S. Cl.
CPC *E04H 3/08* (2013.01); *A61G 3/001* (2013.01); *A61G 12/00* (2013.01); *E04H 1/06* (2013.01);
(Continued)

(58) Field of Classification Search
CPC ......... A61G 3/001; A61G 3/00; A61G 12/00; B60P 3/14; G09B 23/28; E04H 3/08; E04H 1/06; G21F 7/00; A61B 6/56; A61B 6/4441; A61B 6/4464; A61B 6/4452; A61B 6/487; A61N 2005/1094; E04B 1/26
USPC ......... 52/36.1, 173.1, 79.1, 79.4–79.9, 653.1, 52/745.19, 782.1, 796.1, 220.1–220.3, 52/220.5, 220.7–220.8, 514–517; 296/24.1, 24.38, 19, 26, 1.1, 163, 165, 296/168, 171–172, 175, 26.08, 296/26.11–26.15; 89/36.01
See application file for complete search history.

(56) References Cited

U.S. PATENT DOCUMENTS 2,175,671 A * 10/1939 Ryan .......................... 250/517.1
3,827,198 A *  8/1974 Geihl ............................... 52/69
(Continued)

FOREIGN PATENT DOCUMENTS

CH         637444 A5    7/1983
CN       101554853 A   10/2009
(Continued)

OTHER PUBLICATIONS

Stephan Haulon, GE Healthcare: Advantage of Mobile Hybrid Operating Room, You-Tube Video (www.youtube.com/watch?v=CoavgQbRUsM), Dec. 12, 2012.
(Continued)

*Primary Examiner* — Jeanette E Chapman
(74) *Attorney, Agent, or Firm* — Squire Patton Boggs (US) LLP

(57) ABSTRACT

An ambulatory surgical center can include a hybrid operating room. The hybrid operating room can include at least four lead-shielded walls, a floor, and a ceiling. The ambulatory surgical center can also include an imaging device disposed in a central area of the hybrid operating room. The ambulatory surgical center can further include an operating table disposed in the central area of the hybrid operating room. The ambulatory surgical center can additionally include a power room adjacent to the operating room. The power room can include a power supply for the imaging device. The ambulatory surgical center can also include a conduit from the power room to the imaging device configured to deliver power to the imaging device. The ambulatory surgical center can further include an emergency power source for the imaging device configured to permit continuity of surgery in the hybrid operating room during a power outage.

28 Claims, 2 Drawing Sheets

(51) Int. Cl.
*E04H 1/06* (2006.01)
*A61G 3/00* (2006.01)
*A61G 12/00* (2006.01)
*E04B 1/26* (2006.01)
*A61N 5/10* (2006.01)
*A61B 6/00* (2006.01)

(52) U.S. Cl.
CPC ............. *G21F 7/00* (2013.01); *A61B 6/4441* (2013.01); *A61B 6/4452* (2013.01); *A61B 6/4464* (2013.01); *A61B 6/487* (2013.01); *A61B 6/56* (2013.01); *A61N 2005/1094* (2013.01); *E04B 1/26* (2013.01)

(56) References Cited

U.S. PATENT DOCUMENTS

| | | | | |
|---|---|---|---|---|
| 4,074,141 | A | * | 2/1978 | Bryant .................. 250/517.1 |
| 4,149,748 | A | * | 4/1979 | Tanner .................. 296/168 |
| 4,454,905 | A | * | 6/1984 | Banko, Jr. .............. 160/351 |
| 4,827,371 | A | * | 5/1989 | Yost ..................... 361/213 |
| 4,915,435 | A | * | 4/1990 | Levine .................. 296/24.38 |
| 5,207,035 | A | * | 5/1993 | Fowler .................. 52/22 |
| 5,236,390 | A | * | 8/1993 | Young ................... 454/95 |
| 5,345,730 | A | * | 9/1994 | Jurgensen .............. 52/64 |
| 6,039,377 | A | * | 3/2000 | Eberspacher ........... 296/24.38 |
| 6,179,358 | B1 | * | 1/2001 | Hirayama et al. ....... 296/24.38 |
| 7,034,414 | B1 | * | 4/2006 | Foerg et al. ............ 307/150 |
| 7,347,472 | B2 | * | 3/2008 | Pellegrin, Jr. .......... 296/24.38 |
| 7,794,001 | B2 | * | 9/2010 | Blackwell et al. ...... 296/24.38 |
| 8,397,453 | B2 | * | 3/2013 | Shaw .................... 52/232 |
| 8,707,633 | B2 | * | 4/2014 | Han et al. .............. 52/79.5 |
| 8,919,849 | B1 | * | 12/2014 | Robertson ............. 296/24.38 |
| 2005/0136827 | A1 | * | 6/2005 | Basset et al. ........... 454/187 |
| 2006/0010799 | A1 | * | 1/2006 | Bohm et al. ............ 52/236.9 |
| 2007/0033889 | A1 | | 2/2007 | Manzione |
| 2008/0093568 | A1 | * | 4/2008 | Fox et al. .............. 250/515.1 |
| 2009/0001742 | A1 | * | 1/2009 | Chui et al. ............. 296/24.38 |
| 2010/0139179 | A1 | * | 6/2010 | Smith et al. ........... 52/67 |
| 2011/0061317 | A1 | | 3/2011 | Marcus |
| 2011/0277399 | A1 | | 11/2011 | Boekeloo |
| 2012/0265005 | A1 | | 10/2012 | Han et al. |
| 2012/0266379 | A1 | * | 10/2012 | Hushek .................. 5/86.1 |
| 2013/0185090 | A1 | | 7/2013 | Kargar et al. |

FOREIGN PATENT DOCUMENTS

| | | |
|---|---|---|
| CN | 102900249 A | 1/2013 |
| DE | 202012003175 U1 | 5/2012 |
| FR | 595897 A | 10/1925 |
| GB | 2472888 B | 1/2013 |
| WO | 2001012922A A1 | 2/2001 |

OTHER PUBLICATIONS

Ziehm Imaging and Stille: Package Solution for Mobile Hybrid Rooms, press release, Sep. 24, 2012.
International Search Report and Written Opinion of the International Searching Authority for related application PCT/US2015/021236 mailed on Jun. 29, 2015.

* cited by examiner

HYBRID OPERATING ROOM FOR COMBINED SURGICAL AND FIXED IMAGING SERVICES IN AN AMBULATORY SURGICAL CENTER

BACKGROUND

1. Field

Various medical centers, other than hospitals, may benefit from having combined surgical and fixed imaging services. For example, ambulatory surgical centers may benefit from having a hybrid operating room that combines such surgical and fixed imaging services.

2. Description of the Related Art

Combined surgical and fixed imaging services in an operating room have been provided only in hospital facilities. Hospital facilities are generally designed with a variety of special features to fulfill strict safety requirements that add significantly to the cost to build and operate the hospital facility. For example, hospitals are typically constructed to adhere to strict building codes. Hospitals, for example, are classified according to International Building Code (IBC) as Institutional Group I-2, meaning occupancy shall include buildings and structures used for medical care on a 24-hour basis for more than five persons who are incapable of self-preservation. Hospitals typically also have heightened requirements regarding fire control, such as specific required building materials, in part because the occupants of the hospital are often incapable of self-preservation, as noted above.

Furthermore, hospitals traditionally include a variety of equipment. Normally, a hospital includes a number of hospital beds. Similarly, hospitals typically include patient rooms, which may house those hospital beds, and patient restrooms. Often, the size of a hospital is given as the number of beds the hospital has. Furthermore, hospitals also often include other facilities, such as a pharmacy, a lab, a morgue, and facilities providing radiology services, infection isolation, dietary services, linen services, emergency services, and the like.

Additionally, hospitals normally are required to have disaster prevention provisions for the primary structure and services as well as a disaster response plan, policy, and capabilities. Likewise, in view of the size of hospitals, hospitals often include central services (for example, central sterilization services), materials management, environmental services, and engineering services.

According to conventional wisdom, combined surgical and imaging services in an operating room are best provided in a hospital context. For example, imaging equipment is often heavy and has substantial power requirements. Hospitals, with their massive infrastructure, can readily accommodate such requirements. Also, imaging equipment often requires shielding due to the use of radiation, such as x-rays. Again, the infrastructure of a hospital is conventionally thought to be the only medical facility infrastructure adapted to safely accommodate such a purpose. For example, the thick concrete walls and floors of a typical hospital can help to block radiation.

Operating rooms for providing combined surgery and fixed imaging in a hospital are comparatively large. For example, a typical combined surgical and fixed imaging surgery room in a hospital may be in the range of 800 to 1000 square feet. For example, operating rooms in a hospital need to be of such comparatively large size in order to accommodate the performance of up to twenty to thirty different surgical specialties and sub-specialties as may normally be performed in a hospital, such as cardiac, thoracic, vascular, obstetrics, gynecological, orthopedic, podiatric, urologic, otolaryngologic, neurosurgery, trauma, ophthalmology, gastrointestinal, transplant, general surgery, colorectal surgery, hand surgery, endocrine surgery, breast surgery, plastic surgery, head and neck surgery, surgical oncology, pediatric surgery, spine surgery, oral maxillo facial surgery and so on.

Furthermore, hospitals typically are required to have particularly robust infectious vector isolation as well as high quality and sophisticated nurse call systems. Hospitals also have requirements for control of airborne sound transmission and water temperature requirements. Hospitals also normally have medical gas systems with strict requirements on their number and amount of testing. Likewise, elevators in hospitals are required to be large to accommodate gurney traffic.

As mentioned above, hospitals typically have specific fire code requirements. For example, hospital construction materials must be non-combustible and must provide for patient and staff safety in case of an emergency. Because hospitals are viewed as essential in case of a disaster, hospitals must be able to withstand greater events, such as earthquakes, floods, and the like. The structure also needs to be designed to provide the option of defending the structure in place rather than evacuating the structure.

To support such objectives, hospitals may be required to have redundancy of critical services, such as heating, ventilation, and air conditioning (HVAC), power, water supply, water heating, and the like. Furthermore, the materials from which the building is constructed, including the finishes for interior walls and ceilings, must comply with strict fire requirements, such as a very low flame spread index. Other similar reinforcements and protections may likewise be required. In short, a hospital is normally required to have a significantly enhanced infrastructure.

By contrast, conventional ambulatory surgical centers (ASCs) can be constructed in office buildings. These buildings have various code requirements, but typically these requirements are much less strict, and therefore, can be fulfilled with significant cost savings as compared to the cost to build a hospital. For example, an IBC class B structure, which may house an ASC, will have significantly less strict construction requirements than an IBC class I-2 structure, typically associated with the construction of a hospital. Similarly, the air change requirements for ASCs and other requirements may be much less strict for ASCs than for hospitals.

Likewise, ASCs typically do not require a pharmacy, a lab, a morgue, linen services, dietary services, and the like. Indeed, ASCs normally do not have any hospital beds, because it is not expected that the patients will be staying overnight.

Similarly, typical operating rooms in ASCs may be smaller than in hospitals. For example, an operating room in an ASC may be less than 600 square feet and possibly as small as 425 square feet. Furthermore, an ASC may generally offer only one to ten different surgical specialties, rather than the twenty to thirty surgical specialties offered in a typical hospital.

ASCs can herein or otherwise be described in various ways. For example, ASCs can also be referred to as clinics, outpatient surgical centers, and the like. Thus, herein or otherwise the term ASC can refer generally to ASCs, clinics, outpatient surgical centers and similar structures.

SUMMARY

According to certain embodiments of the present invention, an ambulatory surgical center can include a hybrid operating room. The hybrid operating room can include at least four lead-shielded walls, a floor, and a ceiling. The ambulatory surgical center can also include an imaging device disposed in a central area of the hybrid operating room. The ambulatory surgical center can further include an operating table disposed in the central area of the hybrid operating room. The ambulatory surgical center can additionally include a power room adjacent to the operating room. The power room can include a power supply for the imaging device. The ambulatory surgical center can also include a conduit from the power room to the imaging device configured to deliver power to the imaging device. The ambulatory surgical center can further include an emergency power source for the imaging device configured to permit continuity of surgery in the hybrid operating room during a power outage. The ambulatory surgical center can include a wooden frame building structure.

In certain embodiments of the present invention, a method of manufacturing an ambulatory surgical center can include building a hybrid operating room. The hybrid operating room can include at least four lead-shielded walls, a floor, and a ceiling. The method can also include shielding the four walls with lead. The method can further include installing an imaging device disposed in a central area of the hybrid operating room. The method can additionally include installing an operating table disposed in the central area of the hybrid operating room. The method can also include building a power room adjacent to the operating room. The method can further include installing, in the power room, a power supply for the imaging device. The method can additionally include installing a conduit configured to supply power from the power room to the imaging device. The method can also include installing an emergency power source for the imaging device configured to permit continuity of surgery in the hybrid operating room during a power outage. The ambulatory surgical center can include a wooden frame building.

BRIEF DESCRIPTION OF THE DRAWINGS

For proper understanding of the invention, reference should be made to the accompanying drawings, wherein.

DETAILED DESCRIPTION

According to certain embodiments of the present invention, combined surgical and fixed imaging services in an operating room can be provided in an ambulatory surgical center, outpatient surgical center, or the like, which can be collectively referred to as an ambulatory surgical center (ASC).

Figure 1:
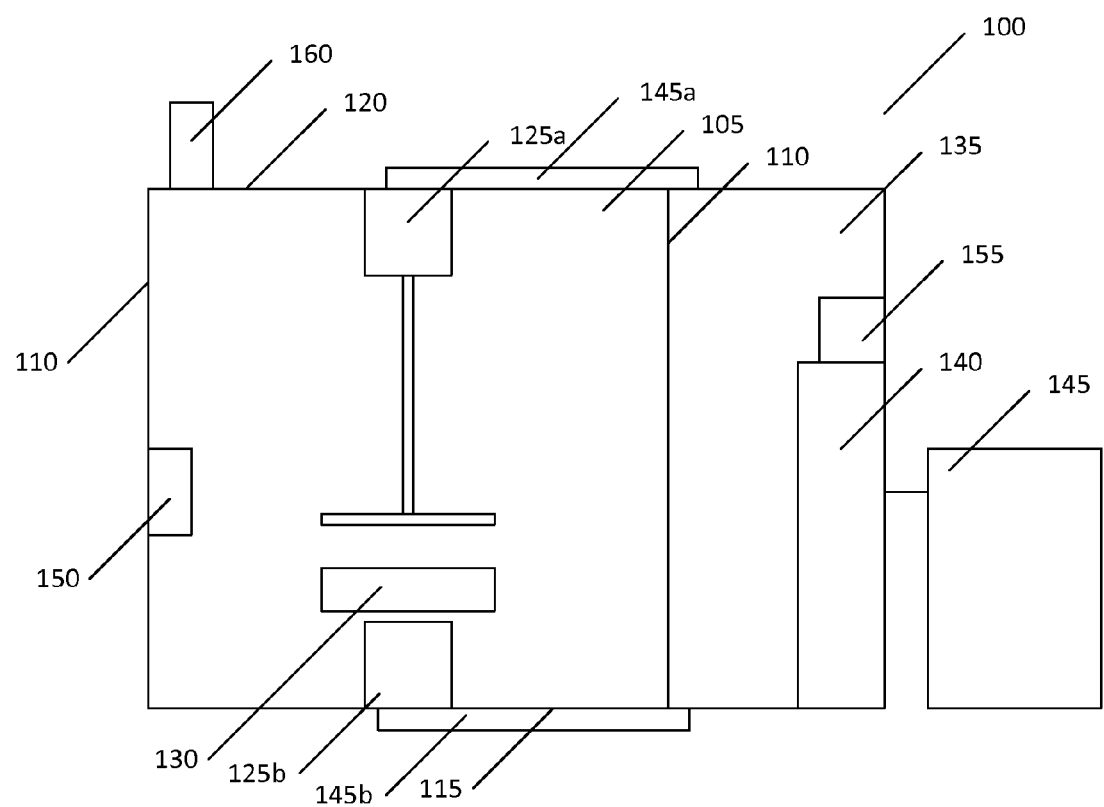
FIG. 1 illustrates a cross-section of an ambulatory surgical center according to certain embodiments of the present invention.

FIG. 1 illustrates a cross-section of an ambulatory surgical center according to certain embodiments. As shown in FIG. 1, an ambulatory surgical center 100 can include a hybrid operating room 105. The hybrid operating room 105 can include at least four lead-shielded walls 110 (only two are shown in the cross-section view, but the other two may be orthogonal to those illustrated), a floor 115, and a ceiling 120. Shielded doors, not illustrated, may also be provided in the lead-shielded walls. Those doors may lead to a hallway or to other rooms.

There can be at least four lead-shielded walls 110, which are shielded to a height of less than a predetermined limit, e.g., eight feet. Thus, the four lead-shielded walls 110 may be shielded to a height that is lower than the height of the ceiling 120. The ceiling 120 may not, in certain embodiments, include lead shielding or any other type of radiation shielding. This may be particularly applicable when the ambulatory surgical center 100 is a single story building or when the ambulatory surgical center 100 is on the top floor of an office building.

The ambulatory surgical center 100 can also include an imaging device 125a, 125b disposed in a central area of the hybrid operating room 105. The ambulatory surgical center 100 can further include an operating table 130 disposed in the central area of the hybrid operating room 105. The operating table 130 is shown without legs due to the cross-sectional view, but the operating table 130 may have legs, wheels, or the like. The operating table 130 may be in a fixed position or may be capable of movement, for example, to position a patient.

The imaging device 125a, 125b can be or include a fluoroscopy device. The fluoroscopy device can include a fixed C-arm device with the ability to perform, among other things, cineradiography (CINE) and digital subtraction. The imaging device 125a, 125b can include a radiating component 125b fixed to the floor 115 or ceiling 120 and a monitor component 125a fixed to the ceiling 120.

The ambulatory surgical center 100 can further include a power room 135 adjacent to the operating room. The power room 135 can include a power supply 140 for the imaging device 125a, 125b. The ambulatory surgical center 100 can include one or more conduit(s) 145a, 145b from the power room 135 to the imaging device 125a, 125b configured to deliver power to the imaging device 125a, 125b.

The conduit(s) 145a, 145b can be located beneath the floor 115 (for example, at 145b), above ground, or above the ceiling 120 (for example, at 145a). An above-ceiling conduit 145a may provide power to elements that are not attached to the floor (such as monitor element 125a), while the below floor-surface conduit 145b can provide power to elements that are attached to the floor (such as radiating component 125b), or which are held in place by gravity.

The power room 135 and/or the power supply 140 can be configured to provide power employing at least 480 VAC. Furthermore, the power room 135 may include a step-up transformer 155 configured to provide the desired power, such as the 480 VAC or any other desired power.

The ambulatory surgical center 100 can additionally include an emergency power source 145 for the imaging device 125a, 125b configured to permit continuity of surgery in the hybrid operating room 105 during a power outage. The emergency power source 145 may be, for example, a generator, an uninterruptable power supply, or another source of power different from the power used in a non-emergency setting.

The ambulatory surgical center 100 can also include equipment 150 configured for the supply and provision of medical gasses. The medical gasses can include anesthetic gasses, such as nitrous oxide, as well as oxygen. The medical gasses equipment 150 can also provide suction. Accordingly, the medical gasses equipment 150 can be attached to plumbing in the wall (not illustrated), as well as to a waste trap (not illustrated). In certain embodiments of the present invention, this plumbing may lead to a central medical gas room, from which gas and suction are provided to a plurality of hybrid operating rooms like hybrid operating room 105.

The ambulatory surgical center 100 can further include an air change system 160. The air change system 160 can be configured to provide a minimum or maximum number of air changes per hour or any desired air change rate therebetween. For example, the minimum number of air changes per hour may, in certain embodiments of the present invention, be six, ten, fifteen, or twenty room air changes per hour or any other desired rate.

The ambulatory surgical center 100 can include a wooden frame building structure. For example, the ambulatory surgical center 100 can be constructed according to building codes that are suitable to an office building. For example, the ambulatory surgical center 100 can be constructed to conform to International Building Code (IBC) Class B standards (or such other standards permitting the use of combustible construction materials).

In certain embodiments of the present invention, the ambulatory surgical center 100 may not be adjacent to or within a hospital. Indeed, in certain embodiments of the present invention, the ambulatory surgical center 100 may not be in close physical proximity to a hospital. Additionally, the ambulatory surgical center 100 may not be affiliated with any hospital.

The ambulatory surgical center 100 may not itself be a hospital. Furthermore, the ambulatory surgical center 100 can exclude an inpatient room configured to permit a patient to stay for more than twenty-three hours. The ambulatory surgical center may not include any rooms equipped with hospital beds. Similarly, the ambulatory surgical center 100 can be operated by medical professionals and medical support staff exclusively dedicated to providing not more than a predetermined number of surgical specialties, e.g., 5 or 10 or any number there between, of medical procedures in the ambulatory surgical center 100. Furthermore, the ambulatory surgical center 100 can be 20,000 square feet or less in terms of its floor space.

Figure 2:
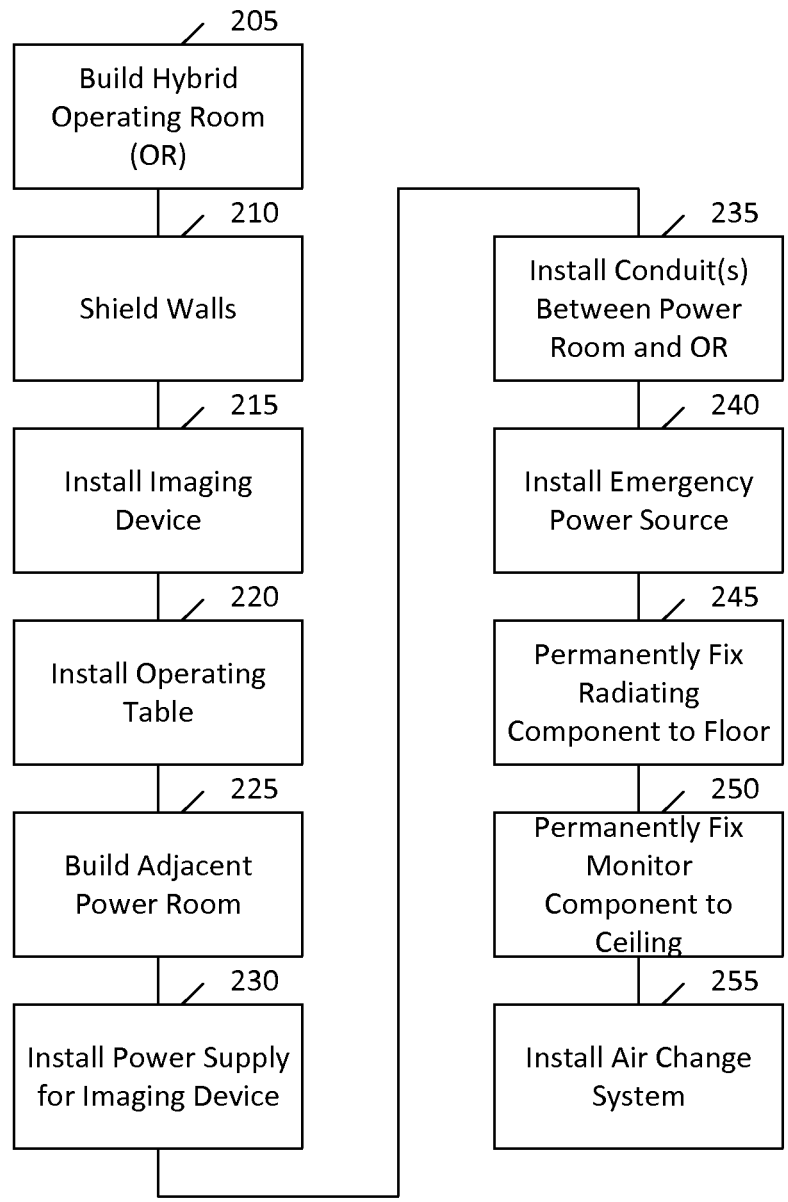
FIG. 2 illustrates a method of manufacturing an ambulatory surgical center, according to certain embodiments of the present invention.

FIG. 2 illustrates a method of manufacturing an ambulatory surgical center, according to certain embodiments of the present invention. The method can include, at 205, building a hybrid operating room. The hybrid operating room can include at least four lead-shielded walls, a floor, and a ceiling. The building of the hybrid operating room can involve converting an existing room into a hybrid operating room through renovations, or can involve building the hybrid operating room during construction of a building housing the hybrid operating room.

The method can also include, at 210, shielding the four walls with lead. The four lead shielded walls can be shielded to a height of less than a predetermined limit, e.g., eight feet. The ceiling can be unshielded. The floor can also be unshielded, for example, when the ambulatory surgical center is on the ground floor of a building that does not have any basement or other space intended for human occupancy.

The method can further include, at 215, installing an imaging device disposed in a central area of the hybrid operating room. The imaging device can be or include a fluoroscopy device. The fluoroscopy device can be a fixed C-arm device.

The method can additionally include, at 220, installing an operating table disposed in the central area of the hybrid operating room. The operating table can be installed and positioned specifically to place a patient within an operational range of the fluoroscopy device.

The method can further include, at 225, building a power room adjacent to the operating room. The building of this power room can be a matter of renovating an existing office building structure, in certain cases.

The method can also include, at 230, installing, in the power room, a power supply for the imaging device. The power supply may be installed to receive electricity from an electric utility company, process it, and supply it to the imaging device. The power room and/or power supply can be configured to provide power at 480 VAC.

The method can additionally include, at 235, installing one or more conduit(s) configured to supply power from the power room to the imaging device. These conduits can be installed beneath the floor of the hybrid operating room and/or in or above the ceiling of the hybrid operating room.

The method can further include, at 240, installing an emergency power source for the imaging device configured to permit continuity of surgery in the hybrid operating room during a power outage. This emergency power source, if it is a generator or a set of batteries, may be installed outside the walls of the ambulatory surgical center, and may be connected by tie-ins to the power room and/or power supply.

The ambulatory surgical center can include a wooden frame building and can be constructed to conform to International Building Code (IBC) Class B standards (or such other standards permitting the use of combustible construction materials), as described above with reference to FIG. 1.

The method can also include, at 245, permanently fixing a radiating component of the imaging device to the floor and, at 250, permanently fixing a monitor component of the imaging device to the ceiling. The monitor component and the radiating component may each include moving parts, but may be anchored to a specific location in the floor and ceiling.

The method additionally may include, at 255, installing an air change system in the ambulatory surgical center, wherein the air change system is configured to provide twenty room air changes per hour (or any other desired rate of air change).

The above method steps are described and illustrated in a particular order. Nevertheless, this order is simply for ease of reading and does not imply that the steps must be performed in the listed order. For example, the installation of the emergency power source may not need to have any particular order with respect to the other steps. Steps that must be performed under the floor, in the walls, or above the ceiling may be performed prior to the installation of the imaging equipment and operating table. Thus, the order of steps may be varied as desired or needed.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

I claim:
1. A stationary ambulatory surgical center, comprising:
   a hybrid operating room, wherein the hybrid operating room includes at least four lead-shielded walls, a floor, and a ceiling;
   an imaging device disposed in a central area of the hybrid operating room;
   an operating table disposed in the central area of the hybrid operating room;
   a power room adjacent to the operating room, wherein the power room includes a power supply for the imaging device;
   an air change system, wherein the air change system is configured to provide from six to twenty room air changes per hour to the hybrid operating room;
   a conduit from the power room to the imaging device configured to deliver power to the imaging device;

an emergency power source for the imaging device configured to permit continuity of surgery in the hybrid operating room during a power outage; and a door connecting the hybrid operating room to at least one hallway;

wherein the ambulatory surgical center includes a wooden frame building structure;

wherein the ambulatory surgical center is housed in a building constructed to conform to International Building Code (IBC) Class B standards; and wherein the ambulatory surgical center comprises 20,000 square feet or less.

2. The ambulatory surgical center of claim 1, wherein the conduit is located beneath the floor, above ground, or above the ceiling.

3. The ambulatory surgical center of claim 1, further including equipment configured for the supply and provision of medical gasses.

4. The ambulatory surgical center of claim 1, wherein the imaging device comprises a fluoroscopy device.

5. The ambulatory surgical center of claim 4, wherein the fluoroscopy device comprises a fixed C-arm device with the ability to perform CINE and digital subtraction.

6. The ambulatory surgical center of claim 1, wherein there are at least four lead-shielded walls which are shielded to a height of less than eight feet.

7. The ambulatory surgical center of claim 1, wherein the ceiling does not include lead shielding or any other type of radiation shielding.

8. The ambulatory surgical center of claim 1, wherein the imaging device comprises a radiating component fixed to the floor and a monitor component fixed to the ceiling.

9. The ambulatory surgical center of claim 1, wherein the ambulatory surgical center is not adjacent to or within a hospital.

10. The ambulatory surgical center of claim 9, wherein the ambulatory surgical center is not in close physical proximity to the hospital.

11. The ambulatory surgical center of claim 10, wherein the ambulatory surgical center is not affiliated with the hospital.

12. The ambulatory surgical center of claim 1, wherein the power room is configured to provide power employing at least 480 VAC.

13. The ambulatory surgical center of claim 12, wherein the power room includes a step-up transformer configured to provide the power employing the at least 480 VAC.

14. The ambulatory surgical center of claim 1, wherein the ambulatory surgical center excludes an inpatient room configured for stay of patients for more than twenty-three hours.

15. The ambulatory surgical center of claim 1, wherein the ambulatory surgical center is operated by medical professionals and medical support staff exclusively dedicated to providing not more than five specialties of medical procedures in the ambulatory surgical center.

16. The ambulatory surgical center of claim 1, wherein the ambulatory surgical center does not include any rooms equipped with hospital beds.

17. The ambulatory surgical center of claim 1, further comprising:

plumbing configured to provide gas and suction, wherein the plumbing leads to a central medical gas room, from which gas and suction are provided to a plurality of hybrid operating rooms.

18. A method of manufacturing stationary ambulatory surgical center, the method comprising:

building a hybrid operating room, wherein the hybrid operating room includes at least four lead-shielded walls, a floor, and a ceiling;

shielding the four walls with lead;

installing an imaging device disposed in a central area of the hybrid operating room;

installing an operating table disposed in the central area of the hybrid operating room;

building a power room adjacent to the operating room;

installing an air change system, wherein the air change system is configured to provide from six to twenty room air changes per hour to the hybrid operating room;

installing, in the power room, a power supply for the imaging device;

installing a conduit configured to supply power from the power room to the imaging device;

installing an emergency power source for the imaging device configured to permit continuity of surgery in the hybrid operating room during a power outage; and installing a door connecting the hybrid operating room to at least one hallway;

wherein the ambulatory surgical center comprises a wooden frame building, wherein the ambulatory surgical center is housed in a building constructed to conform to International Building Code (IBC) Class B standards; and wherein the ambulatory surgical center comprises 20,000 square feet or less.

19. The method of claim 18, wherein the imaging device comprises a fluoroscopy device.

20. The method of claim 19, wherein the fluoroscopy device comprises a fixed C-arm device.

21. The method of claim 18, wherein the four lead shielded walls are shielded to a height of less than eight feet.

22. The method of claim 18, wherein the ceiling is unshielded.

23. The method of claim 18, further comprising:

permanently fixing a radiating component of the imaging device to the floor; and permanently fixing a monitor component of the imaging device to the ceiling.

24. The method of claim 18, wherein the power room is configured to provide 480 V.

25. The method of claim 18, wherein building the hybrid operating room comprises converting an existing room into a hybrid operating room through renovations.

26. The method of claim 18, wherein building the hybrid operating room comprises renovating an existing office building structure.

27. A stationary ambulatory surgical center, comprising:

a plurality of hybrid operating rooms, wherein each of the hybrid operating rooms comprises radiation-shielded walls, a floor, and a ceiling;

an imaging device disposed in a central area of each hybrid operating room;

an operating table disposed in the central area of each hybrid operating room, and a door connecting each hybrid operating room to a hallway;

an air change system, wherein the air change system is configured to provide from six to twenty room air changes per hour to the plurality of hybrid operating rooms;

wherein the ambulatory surgical center is housed in a building constructed to conform to International Building Code (IBC) Class B standards; and wherein the ambulatory surgical center comprises 20,000 square feet or less.

28. A stationary ambulatory surgical center, comprising:
a hybrid operating room, wherein the hybrid operating room includes at least four lead-shielded walls, a floor, and a ceiling;
an imaging device disposed in a central area of the hybrid operating room;
an operating table disposed in the central area of the hybrid operating room;
a power room adjacent to the operating room, wherein the power room includes a power supply for the imaging device;
an air change system, wherein the air change system is configured to provide at least six room air changes per hour to the hybrid operating room;
a conduit from the power room to the imaging device configured to deliver power to the imaging device;
an emergency power source for the imaging device configured to permit continuity of surgery in the hybrid operating room during a power outage; and
a door connecting the hybrid operating room to at least one hallway;
wherein the ambulatory surgical center is housed in a building constructed to conform to International Building Code (IBC) Class B standards; and
wherein the ambulatory surgical center comprises 20,000 square feet or less.

* * * * *